United States Patent
Hokstad et al.

(10) Patent No.: US 11,333,791 B2
(45) Date of Patent: May 17, 2022

(54) METHOD OF CALCULATING RADIOGENIC HEAT PRODUCTION

(71) Applicant: Equinor Energy AS, Stavanger (NO)

(72) Inventors: Ketil Hokstad, Trondheim (NO);
Kenneth Duffaut, Trondheim (NO);
Christine Fichler, Ranheim (NO);
Rune Kyrkjebø, Trondheim (NO);
Zuzana Alasonati Tasarova, Ranheim (NO)

(73) Assignee: EQUINOR ENERGY AS, Stavanger (NO)

( * ) Notice: Subject to any disclaimer, the term of this patent is extended or adjusted under 35 U.S.C. 154(b) by 338 days.

(21) Appl. No.: 16/076,505

(22) PCT Filed: Feb. 20, 2017

(86) PCT No.: PCT/NO2017/050044
§ 371 (c)(1),
(2) Date: Aug. 8, 2018

(87) PCT Pub. No.: WO2017/142422
PCT Pub. Date: Aug. 24, 2017

(65) Prior Publication Data
US 2019/0041546 A1 Feb. 7, 2019

(30) Foreign Application Priority Data
Feb. 19, 2016 (GB) .................................... 1602935

(51) Int. Cl.
*G01V 11/00* (2006.01)
*G01V 9/00* (2006.01)
(Continued)

(52) U.S. Cl.
CPC ............. *G01V 11/00* (2013.01); *G01N 33/24* (2013.01); *G01V 1/282* (2013.01); *G01V 9/00* (2013.01); *G01V 99/005* (2013.01)

(58) Field of Classification Search
CPC .......... G01V 11/00; G01V 1/282; G01V 9/00; G01V 99/005; G01N 33/24
(Continued)

(56) References Cited

U.S. PATENT DOCUMENTS

| | | | |
|---|---|---|---|
| 7,130,758 B2 * | 10/2006 | Srivastava | G06F 17/13 702/136 |
| 2004/0220740 A1 | 11/2004 | Srivastava et al. | |

(Continued)

FOREIGN PATENT DOCUMENTS

| | | |
|---|---|---|
| JP | 2004-292880 A | 10/2004 |
| JP | 2011-508876 A | 3/2011 |

(Continued)

OTHER PUBLICATIONS

Gallagher, Kerry, et al. "The role of thermal conductivity measurements in modelling thermal histories in sedimentary basins." Marine and Petroleum Geology 14.2 (1997).pp. 201-214. (Year: 1997).*

(Continued)

*Primary Examiner* — Kamini S Shah
*Assistant Examiner* — John E Johansen
(74) *Attorney, Agent, or Firm* — Eversheds Sutherland (US) LLP

(57) ABSTRACT

The present disclosure relates to a method of calculating the radiogenic heat production (RHP) of a geophysical structure, wherein there is provided at least one geophysical parameter of the geophysical structure, the method including inverting the at least one geophysical parameter to estimate the RHP of the geophysical structure.

12 Claims, 5 Drawing Sheets

(51) Int. Cl.
*G01V 99/00* (2009.01)
*G01N 33/24* (2006.01)
*G01V 1/28* (2006.01)

(58) Field of Classification Search
USPC .......................................................... 703/10
See application file for complete search history.

(56) References Cited

U.S. PATENT DOCUMENTS

| | | | |
|---|---|---|---|
| 2010/0185422 A1 | 7/2010 | Hoversten | |
| 2010/0326669 A1 | 12/2010 | Zhu et al. | |
| 2015/0242362 A1 | 8/2015 | Wiik et al. | |

FOREIGN PATENT DOCUMENTS

| | | | |
|---|---|---|---|
| JP | 2011-509412 A | 3/2011 | |
| WO | 2014029415 A1 | 2/2014 | |
| WO | 2014173436 A1 | 10/2014 | |

OTHER PUBLICATIONS

Afonso, J. C., et al. "3-D multiobservable probabilistic inversion for the compositional and thermal structure of the lithosphere and upper mantle. I: A priori petrological information and geophysical observables." Journal of Geophysical Research: Solid Earth 118.5 (2013). pp. 2586-2617. (Year: 2013).*

He, Lijuan, Liangping Xiong, and Jiyang Wang. "Heat flow and thermal modeling of the Yinggehai Basin, South China Sea." Tectonophysics 351.3 (2002). pp. 245-253. (Year: 2002).*

Hoover, Donald B., William D. Heran, and Patricia L. Hill. The geophysical expression of selected mineral deposit models. US Department of the Interior, Geological Survey, 1992. pp. 1-136. (Year: 1992).*

Annex to communication for EP 3417321 A1. Jul. 9, 2020. pp. 5. (Year: 2020).*

Nth Office Action for CN 108700675 A. May 17, 2021. pp. 1-8. (Year: 2021).*

Reply to communication from the Examining Division for EP 3417321. dated Oct. 26, 2020. pp. 1-3. (Year: 2020).*

Afonso, J.C., et al., 3-D multiobservable probabilistic inversion for the compositional and thermal stucture of the lithosphere and upper mantle. I: a priori petrological information and geophysical observable, Journal of Geophysical Research: Solid Earth, vol. 118, 2586-2617, doi:10.1002/jgrb.50124, published May 30, 2013 (32 pp.).

Fullea J., et al., LitMod3D: An interactive 3-D software to model the thermal, compositional, density, seismological, and rheological structure of the lithosphere and sublithospheric upper mantel, Geochemistry Geophysics Geosystems, an Electronic Journal of the Earth Sciences, vol. 10, No. 8, Aug. 27, 2009 (21 pp.).

Rybach, L., The Relationship Between Seismic Velocity and Radioactive Heat Prodution in Crustal Rocks: An Exponential Law, Pageoph, vol. 117 (1978/1979), 75-82 (8 pp.).

Extended European Search Report, EP17753556.4, dated Sep. 11, 2019 (11 pp.).

Hodstad, Ketil, et al., Radiogenic heat production in the crust from inversion of gravity and magnetic data, Norwegian Journal of Geology, vol. 97. No. 3, Dec. 13, 2017 (14 pp.).

Rybach, Ladislaus, et al., The Relationship Between Seismic Velocity and Radioactive Heat Productin in Crustal Rocks: An Exponential Law, Pure and Applied Geophysics, Jan. 1978 (9 pp.).

Rybach, Ladislaus, et al., The Variation of Heat Generation, Density and Seismic Velocity with Rock Type in the Continental Lithosphere, Elsevier Science Publishers B.V., Amsterdam, Tectonophysics, 103 (1984) 335 344 (10 pp.).

Afonso, J., Integrated geophysical-petrological modeling of the lithosphere and sublithospheric upper mantle Methodology and applications, Geochemistry Geophysics Geosystems, May 2008 (37 pp.).

Afonso, J.C., et al., 3-D multiobservable probabilistic inversion for the compositional and thermal structure of the lithosphere and upper mantle. I: a priori petrological information and geophysical observables, Journal of Geophysical Research: Solid Earth, vol. 118, 2586-2617, 2013 (32 pp.).

Afonso, J.C., et al., 3-D multiobservable probabilistic inversion for the compositional and thermal structure of the lithosphere and upper mantle. II: General methodology and resolution analysis, Journal of Geophysical Research Solid Earth, vol. 118, 1650-1676, 2013 (27 pp.).

Fullea, J., LitMod3D: An interactive 3-D software to model the thermal, compositional, density, seismological, and rheological structure of the lithosphere and sublithospheric upper mantle, Geochemistry Geophysics Geosystems G3, an Electronic Journal of the Earth Sciences, vol. 10, No. 8, Aug. 27, 2009 (21 pp.).

McKenzie, D., Some Remarks on the Development of Sedimentary Basins, Earth and Planetary Science Letters, 4D (1978), 35-32 (8 pp.).

Rybach, L., The Relationship Between Seismic Velocity and Radioactive Heat Production in Crustal Rocks: An Exponential Law, Pageoph, vol. 117 (1978/1979) (8 pp.).

Hokstad, K., Integrated Basin-scale Thermal Modeling, ResearchGate, Conference Paper—Jun. 2014 (6 pp.).

Mernagh, T.R., et al., A Review of the Geochemical Processes Controlling the Distribution of Thorium in the Earth's Crust and Australia's Thorium Resources, Geosience Australia, May 2008 (59 pp.).

International Search Report and Written Opinion, PCT/NO2017/050044, dated Apr. 28, 2017 (10 pp.).

Kronrod, V.A., et al., Determining Heat Flows and Radiiogenic Heat Generation in the Crust and Lithosphere Based on Seismic Data and Surface Heat Flows, Vernadsky Institute of Geochemistry and Analytical Chemistry, Russian Academy of Science, Geochemistry International, 2006 vol. 44, No. 10, pp. 1035-1040 (6 pp.), Oct. 10, 2005.

Kronrod, V.A., et al., Modeling of the Thermal Structure of Continental Lithosphere, Vernadsky Institute of Geochemistry and Analytical Chemistry, Russian Academy of Science, Physics of the Sold Earth 2007, vol. 43, No. 1, pp. 91-101 (11 pp.), Jun. 28, 2006.

Oliveira, Eara S.L., et al., Radiometric and Thermal Signatures of Turbidite Flows in Namorado Oil Field, CrossMark, Fourteenth International Congress of the Brazilian Geophysical Society, pp. 799-803 (5 pp.), 2015.

Mukai, M. et al., Measurement of radioactive heat generation in rocks by means of gamma ray spectrometry, Vertical distribution of heat source in the island arc crust, Proc. Japan Acad., 75, Ser. B, 1999, pp. 181-185, https://www.jstage.ist.go.jp/article/pjab1977/75/7/75_7_181/_pdf (5 pp.).

Dischler, E. et al., Bayesian anisotropic Dix inversion, SEG Technical Program Expanded Abstracts 2013: pp. 4853-4857, http://library.seg.org/doi/abs/10.1190/segam2013-0098.1 (5 pp.).

GB1602935.7 Search Report, dated Jun. 15, 2016 (4 pp.).

* cited by examiner

METHOD OF CALCULATING RADIOGENIC HEAT PRODUCTION

TECHNICAL FIELD

The present invention provides a method of calculating the radiogenic heat production of a geophysical structure, the basal heat flow and surface heat flow.

BACKGROUND OF THE INVENTION

The variation of subsurface temperature through geological time is of major importance for the petroleum prospectivity of a sedimentary basin. The thermal history controls the maturation of source rocks and the quality of reservoir rocks. The porosity loss associated with quartz cementation is directly dependent on temperature. The thermal regime of a sedimentary basin is controlled by two major factors: basal heat flow with contributions from the Earth's mantle and crust; and the heat conductivity profile of the sedimentary sequence.

The temperature distribution with depth, and through geological time, is determined mainly by the interplay between these first order effects. Thermal modelling is part of basin modelling (Allen and Allen, 2005). Conventional basin modelling is driven by input from the geological disciplines and geochemistry. However, the present method advantageously is driven by geophysical data.

In the prior art, radiogenic heat production (RHP) is typically found by estimating the amount of radioactive elements such as uranium, thorium and potassium (which are major contributors to the RHP) by using spectral gamma-ray logs. For example, in $14^{th}$ International Congress of the Brasilian Geophysical Society, 2015, Oliveira et al, "Radiometric and thermal signatures of turbidite flows in Namorado oil field", pages 799-803, the method taught calculates RHP using a direct measurement of radioactive decay. The method is based on spectral gamma ray logs measured in boreholes. This is a standard approach and uses the empirical equations presented by Rybach (1986). In this method, to obtain separate information about contributions from Uranium, Thorium and Potassium, spectral (frequency dependent) recordings of gamma rays are required, since different elements radiate in different frequency bands.

Alternatively, it is known to manually adjust RHP values to fit temperature data during basin modelling. These methods tend be inaccurate, and require data to be gathered for the specific purpose of calculating RHP.

As another example of the prior art, Geochemistry International, Vol. 44, No. 10, 2006, Kronrod et al, "Determining heat flows and radiogenic heat generation in the crust and lithosphere based on seismic data and surface heat flows", pages 1035-1040, teaches using seismic velocities to estimate the temperature of the crust (using an assumption that the pressure is known and using an equation of state which links pressure and temperature to the seismic velocity). After this, a heat conduction equation is solved to relate the temperature of the crust to surface heat flow and RHP in the crust. Physics of the solid earth, Vol. 43, No. 1, 2007, Kronrod et al, "Modeling of the thermal structure of continental lithosphere", pages 91-101, teaches a broadly similar method.

In one aspect, the invention provides a method of calculating the radiogenic heat production (RHP) of a geophysical structure, wherein there is provided at least one geophysical parameter of the geophysical structure, the method comprising: inverting the at least one geophysical parameter to estimate the RHP of the geophysical structure.

The inventors have found that the RHP of a geophysical structure can be found by inverting at least one geophysical parameter of the geophysical structure, such as density, seismic velocity (preferably seismic p-wave velocity) or magnetic susceptibility. This method is advantageous as it does not require detailed sampling of the geophysical structure to find the RHP throughout the geophysical structure. Rather, since geophysical parameter values can be obtained throughout a geophysical structure by surface measurements and observations, the method of the present invention allows RHP to be calculated using surface measurements and observations.

Unlike the prior art methods mentioned above (such as Oliveira et al. mentioned above), which require the use of gamma ray logs, the present invention can simply rely on geophysical parameter values (which may be already/readily available, and which may be obtained from the Earth's surface rather than in a borehole) to calculate the RHP. Further, unlike the prior art of Kronrod et al mentioned above, which involves numerous intermediate steps in converting seismic velocities into RHP estimations, the present method uses inversion to calculate the RHP directly from the geophysical parameter(s).

The RHP calculated by the present method may preferably be the present-day RHP. This may be the case when a present-day value of the geophysical parameter is used. Of course, if desired historic values could be used to calculated historic RHP. The geophysical structure may preferably be the Earth's crust or lithosphere. The Earth's crust is the layer between the mantle and the surface or sediment layer. The Earth's lithosphere is the layer between the ductile mantle and the surface or sediment layer (i.e. the lithosphere includes the crust and the (mostly) brittle upper mantle). It is particularly useful to calculate the RHP of the crust or lithosphere, as this RHP value can be used to calculate the surface heat flow, as is discussed further below. Calculating the surface heat flow can be used to calculate temperature distributions, which are important in assessing whether the correct conditions for hydrocarbon formation exist, or have existed, in the sedimentary layer or crust.

Inverting or inversion is a well-known term in the art. It describes the process of calculating, from at least one observed/measured parameter, the cause of the parameter (or at least one of the causes of the parameter). Thus, in the present case, physically speaking, the RHP affects the geophysical parameter. However, it is the geophysical parameter that is measured and not the RHP. Calculating the RHP from the geophysical parameter may therefore be described as inverting. The inversion may be considered to be a calculation that uses one or more models (such as rock physics model(s), such as the forward model discussed below, that relates the one or more geophysical parameters to the RHP) to calculate the RHP value directly from the one or more geophysical parameters.

Throughout the specification, terms such as "calculating" and "estimating" are used. These are not intended to be limiting; rather they are merely meant to mean determining or obtaining a value for an actual physical value, such as RHP (or at least a (close) approximation of the physical value).

A geophysical parameter may be any property of the geophysical structure, such as density, magnetic susceptibility, seismic velocity (preferably seismic p-wave velocity), electric conductivity, resistivity or magnetic remanence. Particularly, the geophysical parameter may be a value(s)

describing such a property. Particularly, the geophysical parameter may be any such property that is affected by the RHP.

The inverting step may comprise selecting a forward model that defines a relationship between the at least one geophysical parameter and the RHP of the geophysical structure.

In inversion calculations, a forward model is a relationship between the known/measured parameter (the geophysical parameter in this case) and the unknown quantity (the RHP in this case).

The forward model can be selected based upon expected trends relating the relevant geophysical parameter to RHP. For instance, the geophysical parameter may generally increase or decrease (depending on the geophysical parameter) with increasing RHP. When the geophysical parameter is density or seismic velocity (preferably seismic p-wave velocity) or conductivity, the geophysical parameter may decrease with increasing RHP. When the geophysical parameter is magnetic susceptibility, the geophysical parameter may increase with increasing RHP. The specific forward model used is not essential to the present invention, several such forward models being known in the art, and the skilled person would be aware of which model(s) could be used. Indeed, different forward models can be used to achieve similar results, as long as the forward model is able to model the general trend between geophysical parameter and RHP.

When the geophysical parameter decreases with increasing RHP, the model may be any decaying function. For instance, the geophysical parameter may be proportional to the inverse of the RHP (A) or the (natural) logarithm of the inverse of the RHP i.e. the geophysical parameter $\propto \ln\left(\frac{a}{A}\right)$, or $\propto \frac{1}{A}$, where a is a constant. When the geophysical parameter increases with increasing RHP, the model may be any sigmoid function.

As an illustrative example of a relationship between a geophysical parameter and RHP, Rybach 1978 proposes an exponential relationship between RHP and seismic p-wave velocity ($A(v_p)=ae^{-b \cdot v_p}$), where A is RHP, $v_p$ is seismic p-wave velocity, and a and b are constants. Of course, this is just an illustrative example, and other relationships between RHP and seismic velocity could be used.

Thus, as can be understood from the above, the precise forward model can be selected by the skilled person based upon knowledge of rock physics relations.

Preferably, the model relationship between RHP and the geophysical parameter is not dependent on any other variable, such as any other geophysical parameters. Of course, other constant factors may be present, but there is preferably only one variable. For example, again looking at the exemplary Rybach 1978 relationship between RHP and seismic p-wave velocity, the only variable on which RHP depends is the seismic p-wave velocity. The other factors (a and b) in the equation above of Rybach 1978 are merely constants. As is discussed below, the constant factors may be found by calibration with data.

It should be understood that the model(s) may not show the full complexity of the system, i.e. the model may be intentionally simplified such that the geophysical parameter is dependent only on the RHP. In reality, geophysical parameter(s) generally depend on many variables. However, in the model(s) used in the present method, the geophysical parameter(s) may only depend on the variable of interest; in this case RHP.

There may be provided calibration data comprising at least one measurement of the at least one geophysical parameter and the RHP of the geophysical structure from a sample of the geophysical structure. The method may further comprise obtaining the calibration data. The calibration may preferably contain a plurality of measurements of the at least one geophysical parameter and the RHP of the geophysical structure from a sample of the geophysical structure. The at least one measurement of the at least one geophysical parameter and the measurement of the RHP may preferably have been acquired from substantially the same location in the sample, or may be an overall/average measurement of the sample as a whole.

The inverting step of the method may comprise optimising the forward model based on the calibration data. This optimisation may comprise using the calibration data to find the optimal values of the constant factors in the forward model. Typically, the greater the amount of calibration data, the better the optimisation will be.

Again, looking at the exemplary relationship between a geophysical parameter and RHP set out in Rybach 1978, it is the factors a and b that may be found using the calibration data.

In order to optimise the forward model, it may be assumed that the forward model (which calculates a geophysical parameter from a given RHP), relative to the provided geophysical parameter, has a certain error distribution (i.e. the difference between the provided/observed geophysical parameter and the geophysical parameter calculated by the respective forward model gives an error distribution). Preferably the error distribution is assumed to be a Gaussian error distribution, preferably with zero mean. The forward model is optimised by reducing the error distribution so that it is as small as possible, such as by having a mean of the error distribution to be as close as possible to zero and by having a small a variance of the error distribution as possible. The optimisation may be achieved by finding the value(s) of the constant factor(s) (such a and b in the Rybach 1978 relationship) in the forward model that optimise the forward model.

The optimised forward model can then be used in the inversion to produce a more accurate inversion.

The forward model may be used in the inversion to calculate the probability distribution (and/or the mean and/or variance values (directly)) of the geophysical parameter, given a particular value of RHP (see equation 13 below). This probability distribution function may be used to calculate the probability distribution of RHP (and/or the mean and/or variance values (directly)), given particular values of the geophysical parameter (see equations 4-7 below).

There may be provided at least two geophysical parameters of the geophysical structure. In this case, the method may comprise inverting the at least two geophysical parameters to estimate the RHP of the geophysical structure.

Using at least two geophysical parameters is preferable because doing so may significantly constrain the inversion of the geophysical parameters to RHP. Using only one geophysical parameter to estimate RHP may leave large errors and uncertainties in the calculated RHP. However, as soon as other geophysical parameters are used in the same inversion to calculate the same RHP, the uncertainties dramatically reduce. Indeed, the more geophysical parameters are used, the more accurate the calculated RHP may become. Thus, at least three, four or five geophysical parameters may be used in the inversion. There may be only one, two, three, four or five geophysical parameters used.

The inverting step may comprise using a model in which there is statistical (conditional) independence between the at least two (or three, four, five, etc.) geophysical parameters and statistical dependence between each respective geophysical parameter and the RHP of the geophysical structure.

By "model" here, it may simply mean the mathematical relationships used in the inversion, such as the forward model(s).

The statistical dependence of the RHP on the different geophysical parameters and the statistical (conditional) independence of different geophysical parameters on each other is an important concept that the inventors have discovered. By modelling the inversion problem in this way, it allows for the geophysical parameters and the RHP to be viewed as a network, in which the use of multiple geophysical parameters constrains the values found for the RHP and so reduces errors/uncertainties in the RHP.

Using this assumption, and using such a model, the relationship between the geophysical parameters and the RHP can be described in terms of a Bayesian network, which can be shown on a directed acyclic graph (DAG), such as FIG. 1. Thus, the present inversion may be a Bayesian formulation of the inversion problem. The inversion may be performed in a Bayesian statistical setting.

Expressed differently, the mathematical relationships that are used in the inversion may be selected based on the assumption that the probability of the RHP is separately conditional on each of the respective geophysical parameters, and there is no conditional probability between the geophysical parameters.

It is known in geophysical applications to use a Bayesian approach to the inversion problem. For instance, Afonso 2013a, 2013b teaches using a Bayesian approach. However, there is no teaching of using a Bayesian approach for calculating RHP. For instance, Afonso 2013a, 2013b actually uses RHP as an input to an inversion calculation for estimating the temperature and composition of the mantle. The input value of the RHP in Afonso 2013a, 2013b is merely found by estimating the composition of the geophysical structure and relating the estimated composition to an expected published value of RHP for that composition. In the traditional methods, there is no teaching or suggestion of calculating RHP from geophysical parameters, let alone doing so using multiple geophysical parameters in a statistical network as described above.

The at least two geophysical parameters may comprise at least one electromagnetic geophysical parameter (such as magnetic susceptibility, electric conductivity or resistivity or magnetic remanence) and at least one mechanical geophysical parameter (such as density or seismic velocity (preferably seismic p-wave velocity)). Preferably, at least magnetic susceptibility and density are used, since gravity and magnetic geophysical data (from which magnetic susceptibility and density may be calculated) are commonly available/easy to obtain with 3D coverage over large areas of the Earth. Of course, any combination of magnetic susceptibility, electric conductivity, resistivity, magnetic remanence, density or seismic velocity, preferably seismic p-wave velocity (or any other geophysical parameter on which the RHP is dependent) may be used.

Similarly to the case where only one geophysical parameter may be used in the inversion, when at least two geophysical parameters are used, the inverting step may comprise selecting a forward model for each respective geophysical parameter, the forward models each defining a relationship between the respective geophysical parameter and the RHP of the geophysical structure.

The forward models can be selected based upon expected trends relating the relevant geophysical parameter to RHP. For instance, the geophysical parameters may generally increase or decrease (depending on the geophysical parameter) with increasing RHP. When one of the geophysical parameters is density or seismic velocity (preferably seismic p-wave velocity), the geophysical parameter may decrease with increasing RHP. When one of the geophysical parameters is magnetic susceptibility, the geophysical parameter may increase with increasing RHP. The exact forward model is not essential to the present invention, and the skilled person would be aware of potential models that could be used to model the relationships between the geophysical parameter(s) and the RHP. Indeed, different forward models can be used to achieve similar results, as long as the forward models are able to model the general trend between geophysical parameters and RHP. As an illustrative example of a relationship between a geophysical parameter and RHP, Rybach 1978 proposes an exponential relationship between RHP and seismic p-wave velocity ($A(v_p)=ae^{-b \cdot v_p}$), where A is RHP, $v_p$ is seismic p-wave velocity, and a and b are constants. Of course, this is just an illustrative example, and other relationships between RHP and seismic velocity could be used. Thus, as can be understood from the above, the precise forward model can be selected by the skilled person based upon knowledge of rock physics relations.

Also as has been discussed above, the relationship between RHP and each geophysical parameter is preferably not dependent on any other variable, such as any other geophysical parameter(s). Of course, other constant factors may be present, but there is preferably only one variable. For example, again looking at the exemplary Rybach 1978 relationship between RHP and seismic p-wave velocity, the only variable on which RHP depends is the seismic p-wave velocity. The other factors (a and b) in the equation above of Rybach 1978 are merely constants. The exemplary Rybach 1978 relationship is therefore statistically (conditionally) independent of other geophysical parameters, such as density or magnetic susceptibility. It is therefore suitable for use in the Bayesian network discussed above. Expressed in another way, the only variable in each of such respective forward models is the RHP of the geophysical structure.

It should be understood that the models may not show the full complexity of the system, i.e. the model may be intentionally simplified such that the geophysical parameter is dependent only on the RHP. In reality, geophysical parameters generally depend on many variables. However, in the models used in the present method, the geophysical parameters may only depend on the variable of interest; in this case RHP.

There may be provided calibration data comprising at least one measurement of each of the at least two geophysical parameters and the RHP of the geophysical structure from a sample of the geophysical structure. The method may comprise obtaining the calibration data. The calibration may preferably contain a plurality of measurements of the each of the geophysical parameters and the RHP of the geophysical structure from a sample of the geophysical structure.

The inverting step may comprise optimising the respective forward model(s) based on the calibration data. This optimisation may comprise using the calibration data to find the optimal values of the constant factors in the forward model. Typically, the greater the amount of calibration data, the better the optimisation will be.

Again, looking at the exemplary relationship between a geophysical parameter and RHP set out in Rybach 1978, it is the factors a and b that may be found using the calibration data.

In order to optimise the forward models, it may be assumed that each of the forward models (which calculate a respective geophysical parameter from a given RHP), relative to the respective provided geophysical parameter, has a certain error distribution (i.e. the difference between each provided geophysical parameter and each respective geophysical parameter calculated by the respective forward model gives an error distribution). Preferably the error distribution for each forward model is assumed to be a Gaussian error distribution, preferably with zero mean. The forward models may be optimised by reducing the error distribution so that it is as small as possible, such as by having a mean of the error distribution to be as close as possible to zero and by having a small a variance of the error distribution as possible. The optimisation may be achieved by finding the value(s) of the constant factor(s) (such a and b in the Rybach 1978 relationship) in the forward model that optimise the forward models.

The optimised forward model(s) can then be used in the inversion to produce a more accurate inversion.

Different forward models may be used for each geophysical parameter.

The forward models may be used in the inversion to calculate the probability distribution of each of the geophysical parameters (and/or the mean and/or variance values (directly)), given a particular value of RHP (see equation 13 below). These probability distribution functions can be combined to calculate the probability distribution of RHP (and/or the mean and/or variance values (directly)), given particular values of the geophysical parameters (see equations 4-7 below).

There may be provided at least one type of geophysical data of the geophysical structure, the method comprising inverting the at least one type of geophysical data to calculate the at least one geophysical parameter. Likewise, there may be provided at least two types of geophysical data of the geophysical structure, the method comprising inverting the at least two, three, four or five types of geophysical data to calculate the at least two, three, four or five geophysical parameters.

When the geophysical parameter is density, seismic velocity (preferably seismic p-wave velocity), magnetic susceptibility, electrical conductivity, electric resistivity or magnetic remanence, the geophysical data type may be gravity data, seismic data, magnetic data or magnetotelluric data respectively. The data may be gathered using known techniques, such as seismic data gathering, etc. The method may comprise gathering/obtaining the geophysical data.

Inverting geophysical data to calculate the at least one geophysical parameter can be performed using known techniques, such as single-domain inversion or joint inversion, which may be 2D or 3D inversion. For example, when gravity and magnetic data are to be inverted to density and magnetic susceptibility, a standard Gravmag inversion technique may be used, such as that provided for by the Geosoft software. The skilled person would know numerous inversion methods for inverting geophysical data to geophysical parameters, and these need not be discussed in the present application.

As has been discussed above, the at least one geophysical parameter may be any geophysical parameter which is dependent on RHP, but is preferably independent of, or can be modelled as conditionally independent of, other geophysical parameters, such as density, seismic velocity (preferably seismic p-wave velocity), magnetic susceptibility, electrical conductivity, electric resistivity or magnetic remanence. Any other property of the geophysical structure that can be expressed as a parameter and which is dependent on RHP (and preferably can be expressed as dependent on RHP whilst being independent of any other geophysical parameter/variable) can be used. Any combination of any number of such parameters may be used.

It should be appreciated that the above methods may calculate the RHP for a specific point/location/volume/space of the geophysical structure, said point/location/volume/space corresponding to the point/location/volume/space of the geophysical parameter used in the inversion step (the geophysical parameter(s) used in these methods may be the value of that parameter at a given point/location/volume/space in the geophysical structure). Therefore, in order obtain the spatially dependent RHP function $A(x, y, z)$, the above inversion method may be performed pointwise for each point/location/volume/space in the geophysical structure. As can be appreciated, the geophysical parameter(s) may vary over the space of the geophysical structure, and this may correspond to a spatially varying RHP.

Thus, the method may comprise constructing a spatially dependent RHP function, $A(x, y, z)$. This function may be constructed by calculating the RHP for each point/location/volume/space in the geophysical structure. The RHP may be calculated over substantially the entirety of the geophysical structure, or over a particular area (xy) and depth (z). (As is standard in the art, the x and y axes are mutually perpendicular horizontal directions and the z axis is a vertical direction.)

In another aspect, the invention provides a method of calculating the basal heat flow in a geophysical structure, wherein there is provided a heat flow contribution from the mantle, the method comprising: calculating the RHP of the geophysical structure using any of the above-discussed methods over a space of geophysical structure; summing the RHP of at least some of the space of the geophysical structure; and adding the sum of the RHP to the heat flow contribution from the mantle.

The RHP over a space of the geophysical structure may be the spatial function $A(x, y, z)$ discussed above.

Summing the RHP may comprise summing the RHP over a certain depth range. The depth range may be the depth from the base of the crust (i.e. the depth of the top of the mantle) or the base of the lithosphere (i.e. the depth of the top of the liquid mantle) to a depth above the base of the crust or lithosphere. The depth above the base of the crust or lithosphere may preferably be the top of the crust or lithosphere. Thus, the summing of the RHP may sum the RHP over the entirety of the crust or lithosphere. The summation may be achieved by integrating $A(x, y, z)$ over z between the two depths.

Such a summation of the RHP provides a 2-D heat flow distribution at the upper depth of the summation (e.g. the top of the crust or lithosphere). The 2-D heat flow distribution may be dependent on x and y.

The method may comprise obtaining the mantle contribution to the basal heat flow. The mantle contribution may arise from convection from the mantle. The mantle contribution can be calculated using known techniques and/or known software packages.

The basal heat flow may be present-day basal heat flow.

In another aspect, the invention provides a method of calculating surface heat flow on the Earth's surface, wherein there is provided a sediment contribution to the surface heat flow, the method comprising: calculating the basal heat flow using any of the above-described method(s), wherein the geophysical structure is the crust or lithosphere and the basal heat flow is calculated at the top of the crust or lithosphere; and adding the sediment contribution to the basal heat flow.

Sediment is a layer which may or may not be present on the Earth's surface, on top of the crust/lithosphere. If the sediment layer is not present, then the method of calculating the basal heat flow can calculate the surface heat flow, without the need for taking into account any sediment contribution (or alternatively, it could be considered that in this case the sediment contribution is zero).

The sediment layer may produce heat due to radioactive elements in the sediment. The sediment contribution is typically considered to be around 1 $\mu Wm^{-3}$. The method may comprise calculating the sediment contribution. The contribution to the surface heat flow at a given surface location can be found by multiplying the depth of the sedimentary layer at that surface location by 1 $\mu Wm^{-3}$.

The surface heat flow may preferably be present-day surface heat flow (if present-day data is used in the calculation), but may also be historic heat flow (if historic data is used).

The surface heat flow may be used to obtain an estimate of the present-day temperature distribution and the maximum paleo temperature of the geophysical structure, preferably in the steady-state approximation. The skilled person would be aware of techniques to perform this calculation.

The steady state approximation is an assumption that the thermal state (heat flow and temperature distribution) does not change with time. In the steady state approximation, temperature is given by Fourier's law, q=k dT/dz in the 1D case. Then, given thermal conductivity (k) and heatflow (q), the temperature as function of depth can be computed by integration of Fourier's law.

If the system is time dependent (i.e. not steady state), it is in general out of thermal equilibrium, and the temperature distribution may be computed by solving a time-dependent diffusion equation (which can be derived combining Fourier's law with the principle of conservation of energy).

The method may also comprise modelling the thermal history of the geophysical structure. For thermal history modelling, the present-day heat flow can be used as an aiming point for kinematic restoration and heat flow history modelling.

In another aspect, the invention provides a method of producing a heat and/or temperature model of a geophysical structure comprising the method of any of the preceding claims.

As can be appreciated, the above methods be used when prospecting for hydrocarbons, e.g. when planning and performing (prospective) drilling operations. The method may further comprise using the calculated RHP, the surface heat flow, the temperature, or heat/temperature model to prospect for hydrocarbons.

In another aspect, the invention provides a computer program product comprising computer readable instructions that, when run on a computer, is configured to cause a processer to perform any of the above methods.

BRIEF DESCRIPTION OF THE DRAWINGS

Preferred embodiments of the invention will now be discussed, by way of example only, with reference to the accompanying drawings, in which:

FIG. 1 shows that the RHP, A, is dependent on radioactive elements such as Th, U and K.

DETAILED DESCRIPTION OF THE INVENTION

As is shown in the exemplary method below, the estimation of basal and surface heat flow is addressed, preferably using inversion of at least two geophysical parameters. As a general workflow of this method, firstly geophysical parameters are obtained by single-domain or joint inversion (e.g. of gravity and magnetics, optionally seismic data). This may be 2D or 3D inversion. Secondly, the geophysical parameters (such as density, magnetic susceptibility and optionally seismic velocity) are inverted to obtain radiogenic heat production (RHP) using crustal rock physics relations. Present-day heat flow is obtained by combining RHP with the mantle contribution to the heat flow. To compute the mantle part of the heat flow, the LitMod3D software, developed by Afonso et al. (2008) and Fullea et al. (2009), may be used.

The estimated basal and surface heat flow can be applied directly to compute temperature within the steady-state approximation. For thermal history modelling, the present-day heat flow can be used as an aiming point for kinematic restoration and heat flow history modelling. There are techniques known in the art for achieving such kinematic restoration (McKenzie 1978).

Thus, in the present disclosure a work flow is presented, where the characteristic features of RHP are utilized to obtain estimates of the present-day crustal RHP from inversion of geophysical data and geophysical parameters. In the example below, three types of geophysical data are considered: magnetic data, gravity data, and seismic data. Most important for regional studies are gravity and magnetic data, which are commonly available with 3D coverage over large areas. Magnetotelluric (MT) data, magnetic remanence and resistivity could also be included. From the geophysical data, magnetic susceptibility, density and seismic p-wave velocity are obtained by inversion. For the seismic case the term inversion should be understood as either tomography or full-waveform inversion. For the magnetic and gravity data, the inversion is a Gravmag inversion, constrained on geometry.

In the exemplary method below, radiogenic heat production (RHP), present-day basal heat flow and surface heat flow are computed from geophysical inversion.

Figure 1:
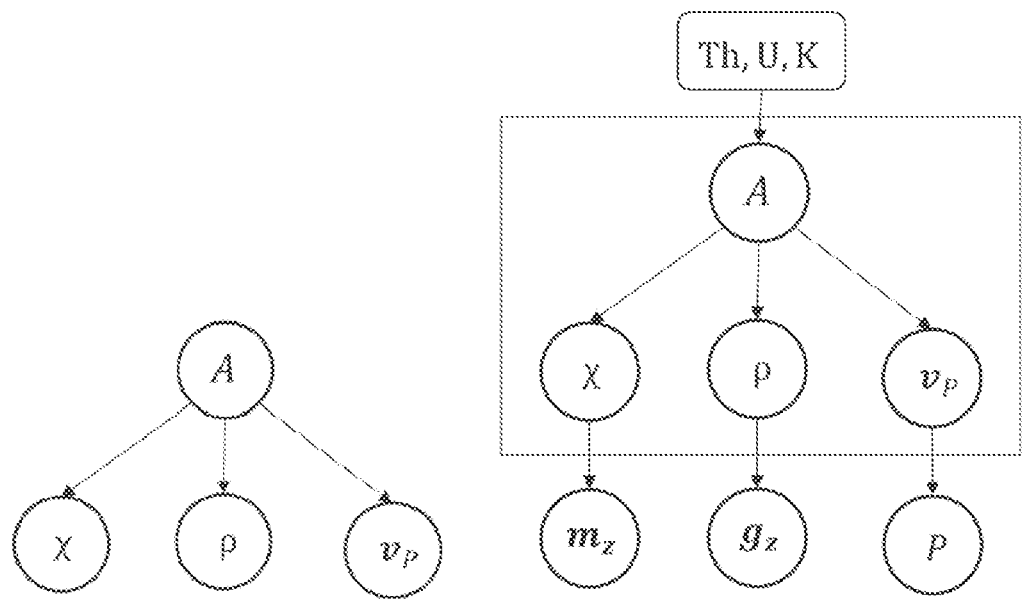
FIG. 1 shows a Bayesian network (a DAG) representing the model relationship between radiogenic heat production A and geophysical parameters $\{\chi, \rho, v_p\}$. As shown on the right-hand side of FIG. 1, the geophysical parameters can also depend on other parameters, such a geophysical data (like gravity data ($m_z$), magnetic data ($g_z$) and seismic data (P)) which can be included in an extended Bayesian network. In the method set out below only the simpler statistical model is considered. Further.

The RHP is due to the occurrence of long-lived isotopes of Th, U and K in crustal rocks. In the present method, it is assumed that the relationship between geophysical data and RHP can be modelled in terms of the Bayesian network, or directed acyclic graph (DAG), shown in FIG. 1.

The joint probability distribution for a Bayesian network is defined by the marginal distributions of the parent nodes and the conditional distributions for the children. The joint distribution for variables $(x_i, \ldots, x_n)$ is then given by $$p(x_i, \ldots, x_n) = \prod_i p(x_i | x_i^{Pa}), \quad (1)$$

where $x_i^{Pa}$ denote parent nodes. The top nodes of the network have no parents. Applying the general Bayesian factorization rule, Equation 1, to the DAG in FIG. 1, the joint probability of RHP and geophysical parameters can be written as $$p(A, m_1, \ldots, m_n) = \prod_i^n p(m_i | A) p(A; \lambda) \quad (2)$$

where $m = \{\chi, \rho, \nu_p\}$, $\chi$ is magnetic susceptibility, $\rho$ is mass density, $\nu_p$ is P-wave velocity, and A is RHP. The dimension of RHP is $\mu W/m^3$. The prior distribution $p(A; \lambda)$ depends on the hyperparameter $\lambda$, to be discussed later. Electric resitivity could also have been included in m. Using conditional independence of parameters $m_i$, the joint distribution in Equation 2 can also be written as $$p(A, m_1, \ldots, m_n) = p(A | m_1, \ldots, m_n) \prod_{i=1}^n p(m_i), \quad (3)$$

from equations 2 and 3 the posterior distribution for the RHP can be obtained, $$p(A | m_i, \ldots, m_n) = \prod_{i=1}^n \frac{p(m_i | A)}{p(m_i)} p(A; \lambda), \quad (4)$$

and substituting the actual parameters for $m_i$ gives the following equation, $$p(A | \chi, \rho, \nu_p) = \frac{p(\chi | A) p(\rho | A) p(\nu_P | A) p(A; \lambda)}{p(\chi) p(\rho) p(\nu_p)}. \quad (5)$$

When the posterior distribution of A is known, the posterior expectation and posterior variance is given by $$\mu_{A|\chi,\rho,\nu p} = \int A p(A | \chi, \rho, \nu_p) dA, \quad (6)$$

$$\sigma_{A|\chi,\rho,\nu p}^2 = \int [A - \mu_{A|\chi,\rho,\nu p}]^2 p(A | \chi, \rho, \nu p) dA. \quad (7)$$

It is equations 4-7 that are most useful for calculate the likely RHP for given geophysical parameters. However, as is clear from equation 4 and 5, in order to do so, it is necessary to know the likelihood functions $p(m_i | A)$ for each of the geophysical parameters $m_i$. Further it is necessary to know the prior distribution $p(A; \lambda)$. Methods of calculating these are given below.

Regarding the prior distribution $p(A; A)$, in the present method it is assumed to be Gaussian, $$A \sim \mathcal{N}(\mu_A(\lambda), \sigma_A^2(\lambda)), \quad (8)$$

where $\mu_A$ and $\sigma_A^2$ are the prior expectation and variance, respectively. The prior distribution incorporates the user's prior knowledge regarding the RHP, for instance that the RHP is usually within a relatively narrow range, $0 < A < 10$ $\mu W/m^3$. The hyperparameter A reflects the user's prior knowledge about the geological or petrological setting, for instance the user knows that the average RHP is always higher in continental crust than in oceanic crust, and is typically, $\mu_A \sim 2$ $\mu W/m^3$ for felsic rocks, and $\mu_A \leq 1$ $\mu W/m^3$ for mafic rocks. If the user's prior knowledge is sparse, the prior variance $\sigma_A$ should be correspondingly large.

Thus, the prior distribution may preferably be a statistical distribution, preferably a Gaussian distribution. Preferably, the mean and variance of the prior distribution is selected by the user based on the user's prior knowledge of the geophysical structure in question (e.g. whether the geophysical structure is oceanic or continental crust, and knowledge of typical variances of RHP).

For the likelihood functions $p(m_i | A)$ on the right-hand side of Equations 4 and 5, these are calculated using forward models $F_i(A)$. The forward models are mathematical relationships that compute the relevant geophysical parameter $m_i$ for a given RHP A. Regarding the present method, it is assumed that each of the forward models $F_i(A)$ have respective Gaussian error distributions with zero mean, when compared with the respective measured/observed geophysical parameters, i.e.

$$m_i - F_i(A) = e_i \sim \mathcal{N}(0, \sigma_{ei}^2), \quad (9)$$

where $\sigma_{ei}$ is the error variance.

As discussed in detail above, the particular forward models used are not essential to this invention and the skilled person would be aware of suitable forward models to use. For example, when the geophysical parameter is the seismic P-wave velocity, a forward model could be one with logarithmic dependence on RHP, as disclosed in Rybach, 1978, $$F_v(A) = \frac{1}{b}\ln\frac{a}{A} \qquad (10)$$

Corresponding forward functions can be found for the other geophysical parameters, each forward function relating RHP A to the respective geophysical parameters. For instance, for density, seismic velocity and/or conductivity any decaying function, such as $$\text{the geophysical parameter} \propto \ln\left(\frac{a}{A}\right), \text{ or } \propto \frac{1}{A},$$

may be used. For susceptibility any sigmoid function may be used.

As can be appreciated from equation 10, the forward functions may be controlled by constant factors (such as a and b in equation 10). In the present method, these constant factors may be determined from calibration data, which may be measured on rock samples, which may be taken from the geophysical structure. Given a set of N rock sample measurements $\{m_i^j, A^j\}$, where j denotes the sample number, of geophysical parameter $m_i$ and RHP A, and the forward model $F_i(A)$, the standard estimators for the expectation and variance of the Gaussian error in equation 9 can be found respectively as, $$\hat{\mu}_{ei} = \frac{1}{N}\sum_{j=1}^{N}\left[\hat{m}_i^{(j)} - F_i(\hat{A}^{(j)})\right], \qquad (11)$$

$$\hat{\sigma}_{ei}^2 = \frac{1}{N-1}\sum_{j=1}^{N}\left[\hat{m}_i^{(j)} - F_i(\hat{A}^{(j)}) - \hat{\mu}_{ei}\right]^2. \qquad (12)$$

Figure 2:
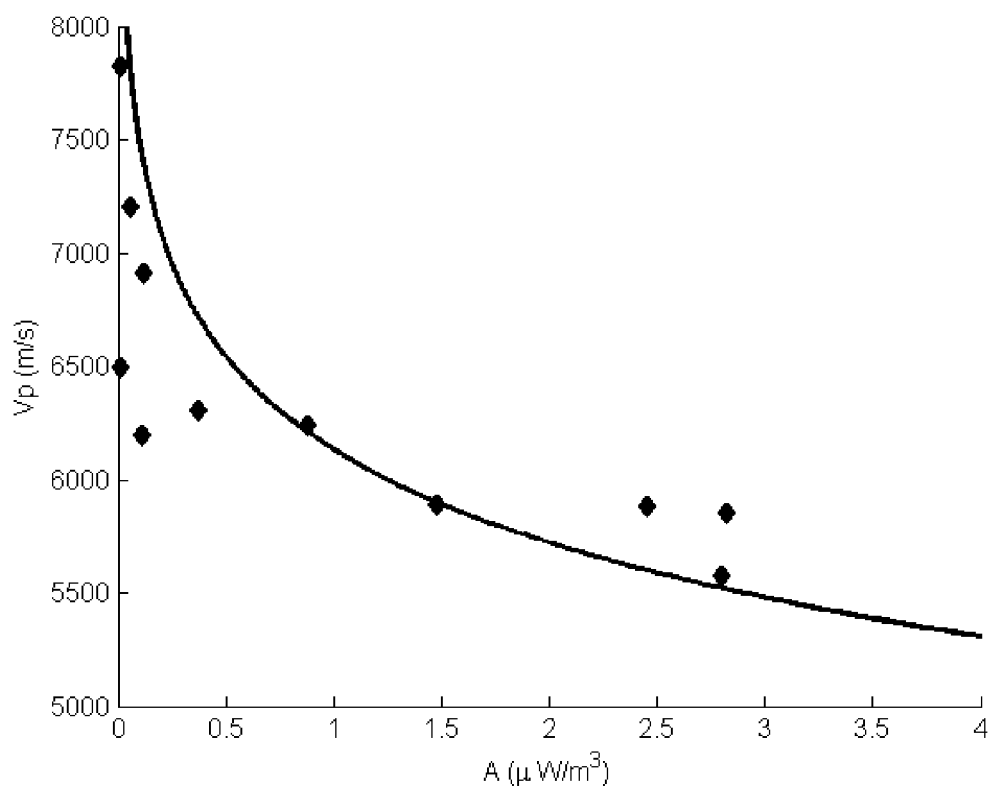
FIG. 2 shows a rock physics forward model and calibration data. The forward model is the logarithmic model of equation 10 (the line shown in FIG. 2) relating seismic velocity $v_p$ with RHP A, and has been calibrated using the calibration data (the data points shown in FIG. 2).

The optimal parameters (such as $v_\infty$, $v_0$ and $\beta$ in equation 10) such that $\sigma_{ei}^2$ is minimum and $\mu_{ei} \approx 0$. These may be found using any known mathematical technique for optimising, such as regression. FIG. 2 shows an example of the logarithmic forward model for P-wave velocity and RHP (the line) after it has been calibrated using calibration data (the data points).

Once the optimal parameters for the respective forward models have been found by calibration, the maximum likelihood functions (i.e. the maximum likelihood of a geophysical parameter given a value of RHP, $p(m_i|A)$ in equations 4 and 5) are given explicitly by $$p(m_i|A) = \frac{1}{\sigma_e\sqrt{2\pi}}e^{-\frac{[m_i-F_i(A)]^2}{2\hat{\sigma}_{ei}^2}} \qquad (13)$$

These maximum likelihood functions, together with the prior distribution discussed above are used in equations 4-7 to calculate the posterior distribution for the RHP given the measured/obtained geophysical parameters, $p(A_{|\chi, \rho, v_p})$, the posterior expectation and the posterior variance. It is in this way that the RHP is calculated, i.e. these quantities give the useful values of RHP, which may be used to calculate basal heat flow, surface heat flow and temperature distribution.

It should be appreciated that with a Bayesian formulation of the inversion problem, the present method honours the fact that the proposed crustal rock physics models (the forward models) do not perfectly describe the observations (calibration data). This imperfectness is accounted for by the error variance $\sigma_{ei}$ in the likelihood distributions given in Equation 13. This in turn provides a quantitative estimate of the posterior variance $\sigma_{A|\chi, \rho, \sigma_p}^2$ of the RHP obtained by the rock-physics inversion. Thus, Equation 3 is effectively a univariate distribution for A, with posterior mean and posterior variance given by Equations 6 and 7.

It should also be appreciated that the above-described steps may merely have calculated RHP, A, for a specific point in the geophsical structure. This point is the location corresponding to the location of the value of the respective geophysical parameters that are used to calculate the RHP. Thus, preferably, all the geophysical parameters that are used in the above steps are taken from the same, or at least similar, locations in the geophysical structure.

In order to construct a view of RHP over a region, or the entirety, of the geophysical structure, the above steps for calculating A are be carried out for different locations in the geophysical structure. However, the calibration of the forward models may only be carried out once, i.e. it need not be carried out for each different location. In some circumstance, the calibration may be carried out for each location.

Thus, the above-discussed rock physics inversion is thus applied pointwise to obtain the spatially varying RHP A(x, y, z).

Once A(x, y, z) has been found, the basal heat flow can be found. As mentioned above, the basal heat flow (which may be the heat flow at the top of the crust) consists of two major parts: the contribution from RHP in the crust; and the contribution from mantle convection. The crustal part can be approximated by integration of A(x, y, z) over the depth z of the crust (e.g. from Top Crust $Z_T$ to Base Crust $Z_B$). The basal heat flow can be found by adding contributions from the crust (RHP) and mantle (convection) to obtain basal heat flow. The basal heat flow is thus given by $$q_B(x,y) = q_M + \int_{Z_T}^{Z_B} A(x,y,z)dz, \qquad (14)$$

where $q_M$ is the contribution from the mantle. The contribution from the mantle can be found using known techniques, such as using LitMod3D software.

Further, once the basal heatflow has been found, an approximation for the surface heat flow $q_0$ can be obtained by adding the contribution to surface heat flow from sediments to the basal heat flow. For example, surface heat flow can be found by adding the average sediment heat production to the basal heat flow, $$q_0(x,y) = q_B(x,y) + (Z_T - Z_S)\bar{A}_S(x,y,z), \qquad (15)$$

where $Z_T - Z_S$ is the thickness of the sedimentary package, and $A_S \sim 1$ μW/m². $Z_T$ may be between 0 and around 20 km depth from the surface, depending on the location. $Z_S$ is the depth of the upper part of the sediment layer, which may be zero on land or may be the depth of the seabed at sea. $Z_B$ may be the depth to the Moho or to the top lower crust (which may be around ⅔ between the top crust and the Moho).

Further still, from the surface heat flow, the present day temperature and the maximum paleo temperature of the geophysical structure (e.g. of the crust/lithosphere and optionally the sediment layer) can be found using the steady-state approximation.

Thus, the above steps set out an exemplary workflow for calculate the RHP, the basal heat flow, the surface heat flow and the temperature of a geophysical structure, in accordance with the present invention.

The following is a numerical example in which the above-discussed method was implemented on measured data. This example shows the effectiveness of the present method, and in particular how the use of multiple geophysical parameters improves the inversion calculation for finding the RHP.

Figure 3:
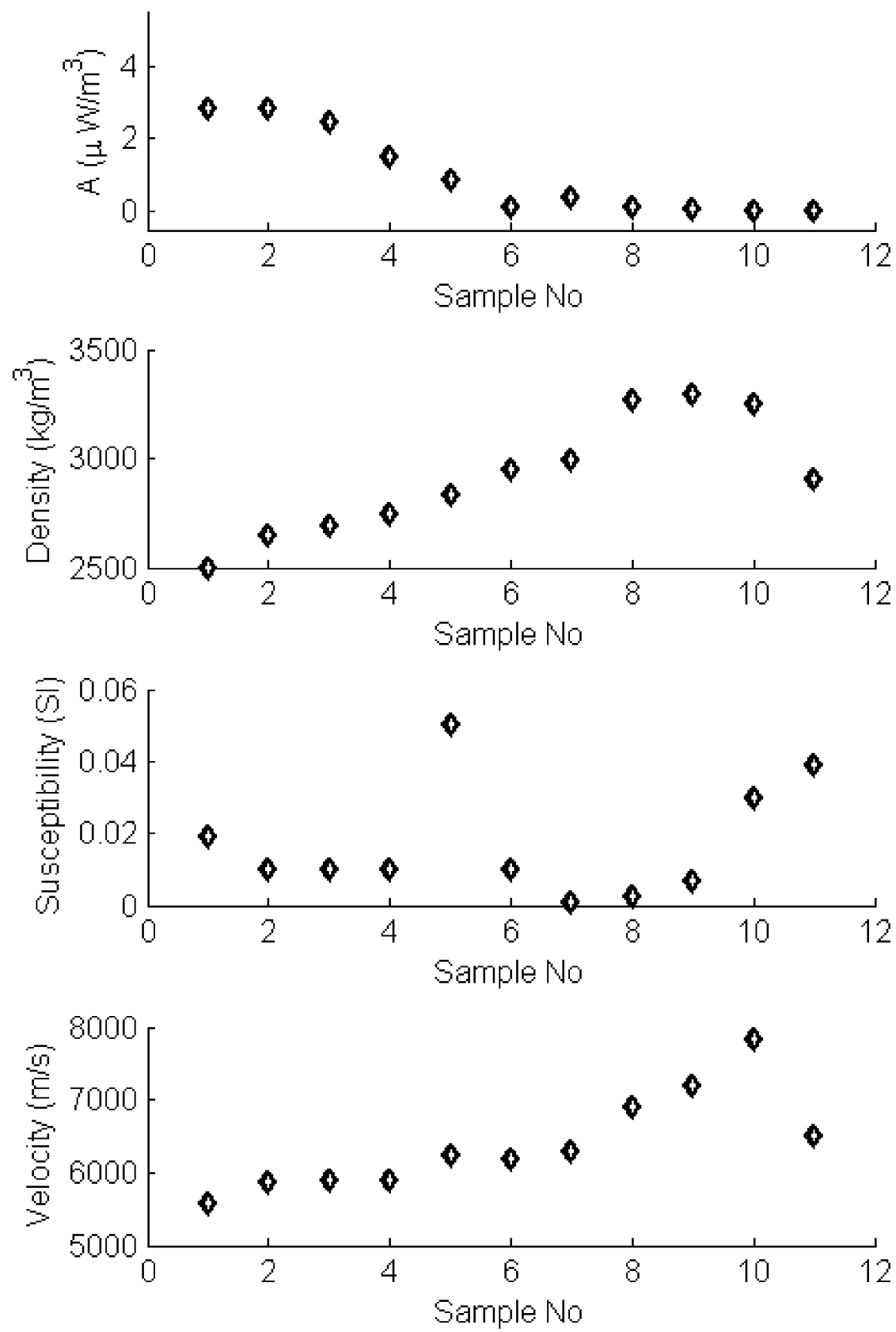
FIG. 3 shows data samples with measured RHP (top) density (second from top), susceptibility (second from bottom) and seismic velocity (bottom). These data samples are used to show the effectiveness of the present method.

Regarding FIG. 3, this shows the measured values of RHP (A) and a number of geophyscial parameters (density, magnetic susceptibility, and seismic velocity). (Incidentally, such measured values of sample could also be used to calibrate the forward models as mentioned above). 11 samples of the geophysical parameters are shown.

The aim of the numerical test is to show that, by using the present inversion method, the RHP can be accurately calculate from the geophysical parameters.

Figure 4:
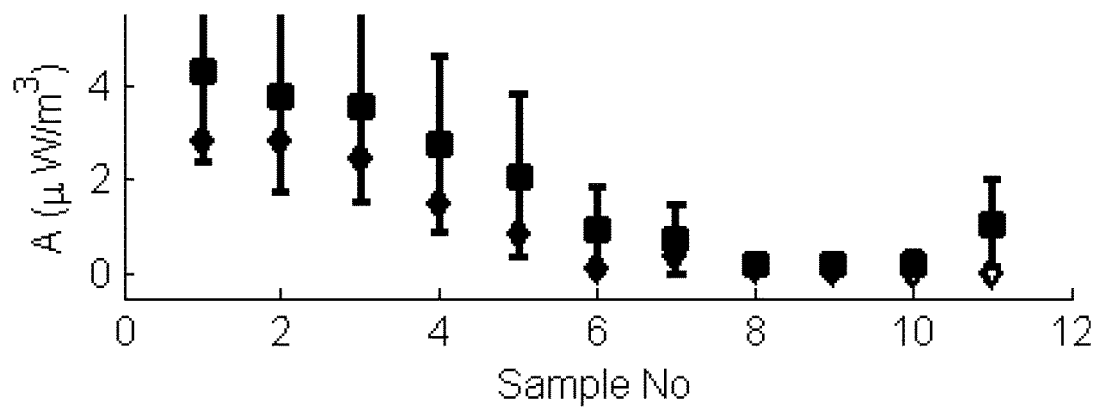
FIG. 4 shows the results of the Bayesian rock-physics inversion of the present disclosure on the data in FIG. 3. In the top graph, the RHP is calculated using density only. In the middle graph, RHP is calculated using density and susceptibility only. In the bottom graph, RHP is calculated using density, susceptibility and seismic velocity. The measured RHP values for each sample are given in diamond dots, and the calculated RHP values for each sample are given in square dots. The square dots show the posterior mean $\mu_{A|\chi, \rho, v_p}$, and the error bars are given by $\mu_{A|\chi, \rho, v_p} \pm \sigma_{A|\chi, \rho, v_p}$.
Figure 4:
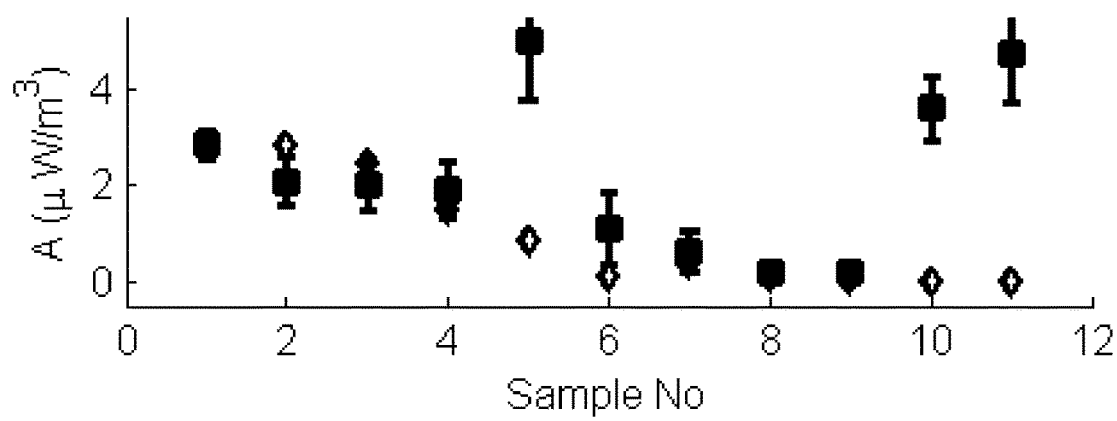
Figure 4:
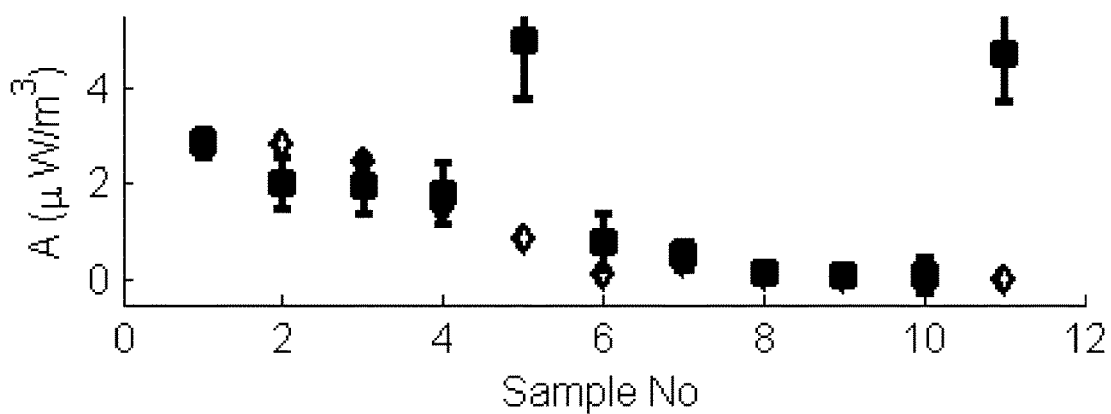

FIG. 4 shows the results from three different test runs of the present estimation method. In the first test run (the top graph), only one geophysical parameter is used (density only). In the second test run (the middle graph), two geophysical parameters are used in a Bayesian setting (density and magnetic susceptibility only). In the third test run (the bottom graph), three geophysical parameters are used in a Bayesian setting (density, magnetic susceptibility and seismic velocity only). The square dots show the posterior mean $\mu_{A|\chi, \rho, v_p}$, and the error bars are given by $\mu_{A|\chi, \rho, v_p}$.

As can be seen, using only one geophysical parameter in the inversion, the general trend is correct, discriminating samples with higher and lower RHP, and the measured RHP is within the error bars of the inversion. However, the error bars are quite large and some of the mean values are quite distant from the actual values of the RHP samples (the diamond dots). Quantitatively, the inversion result is far from the measured values for the samples with large RHP. Thus, it appears that inversion of density alone can detect very low RHP (due to high density), but cannot capture well the quantitative value of samples with high RHP.

However, as can be seen from the lower two graphs, on the whole the accuracy of the mean and the size of the variance of the RHP can be dramatically improved by using two, or preferably three, geophysical parameters. The improvement occurs due to better constraining of the RHP distribution using multiple geophysical parameters.

Figure 5:
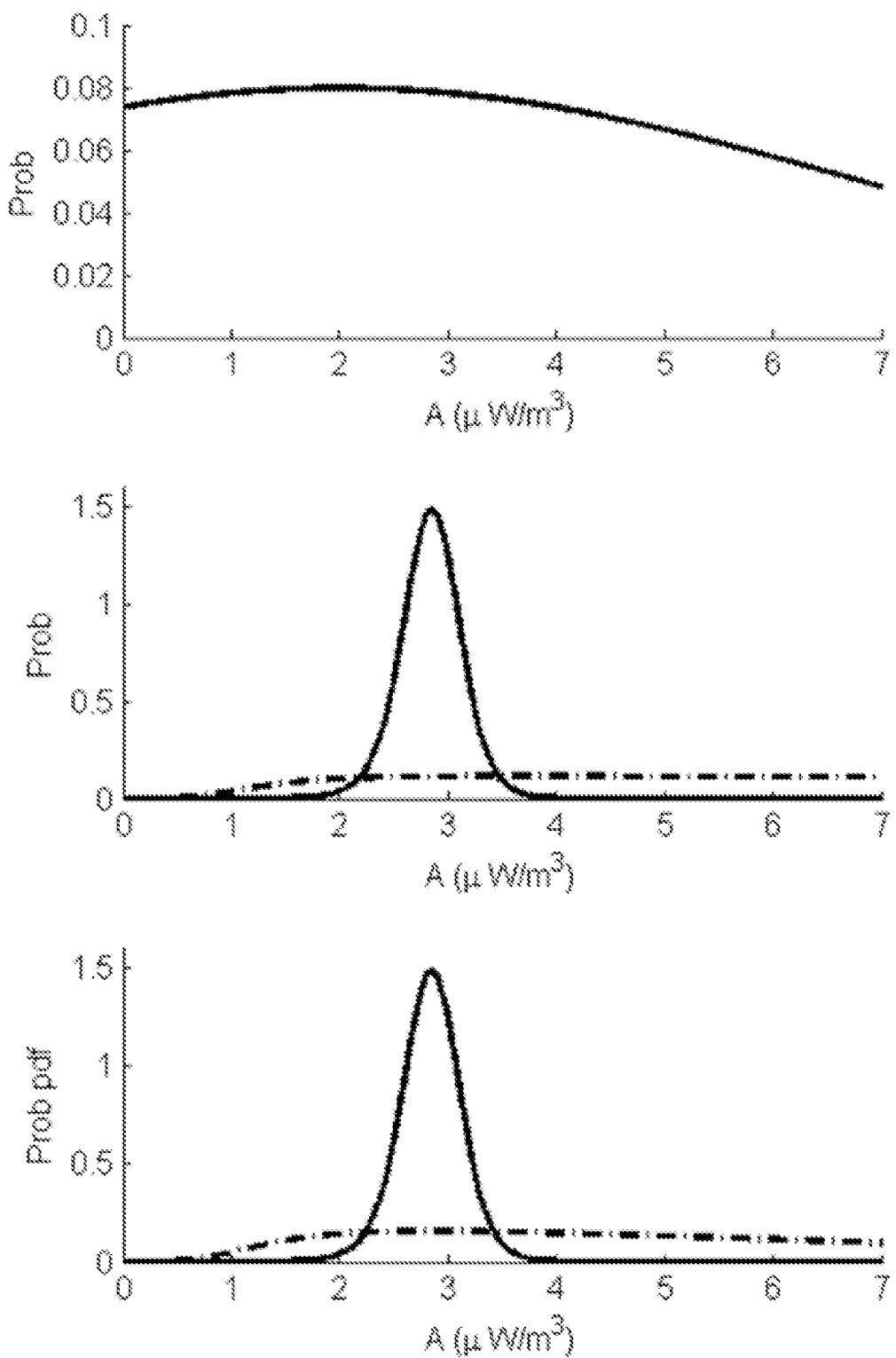
FIG. 5 shows probability densities of RHP calculated from the Bayesian rock-physics inversion of present disclosure on Sample 1 in FIG. 3. In the top graph, the prior distribution is shown. In the middle graph, the likelihood distribution is shown. In the bottom graph, the posterior distribution is shown. In the middle and the bottom graphs, the distributions are calculated by inversion of density only (dot-dashed line), density and susceptibility (solid line) and density, susceptibility and seismic velocity (solid line) (for Sample 1, the distributions for density and susceptibility and density, susceptibility and seismic velocity substantially overlap one another, so only two lines in total can be seen).
Figure 6:
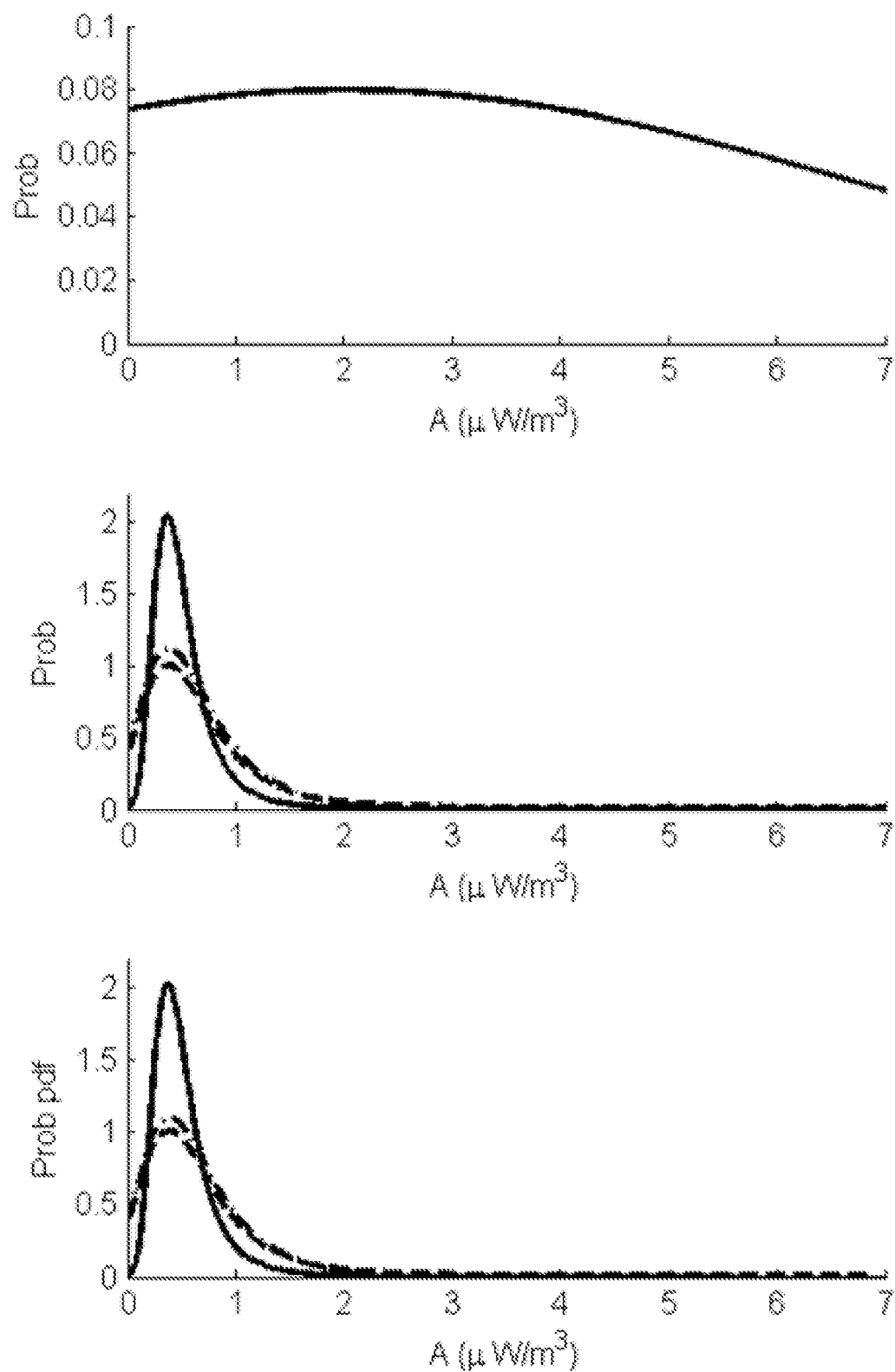
FIG. 6 probability densities of RHP calculated from the Bayesian rock-physics inversion of present disclosure on Sample 7 in FIG. 3. In the top graph, the prior distribution is shown. In the middle graph, the likelihood distribution is shown. In the bottom graph, the posterior distribution is shown. In the middle and the bottom graphs, the distributions are calculated by inversion of density only (dotted line), density and susceptibility (dot-dashed line) and density, susceptibility and seismic velocity (solid line).

This improvement is further illustrated in FIGS. 5 and 6. FIGS. 5 and 6 show the prior (top graph), likelihood (middle graph) and posterior (bottom graph) distributions of the RHP calculated by the present inversion method using data from Sample 1 (FIG. 5) and Sample 7 (FIG. 6) taken from FIG. 3. The two samples are representatives of the two main cases we want to discriminate: relatively high RHP (Sample 1, FIG. 5) and low RHP (Sample 7, FIG. 6).

As can be seen from the top graph of both FIGS. 5 and 6, the prior distribution is wide (non-informative), and does not heavily steer the inversion.

As can be seen from the middle graph of FIG. 5, the likelihood distribution for RHP is initially very wide (dot-dashed line) when only one geophysical parameter (density) is used. However, when two or three geophysical parameters (density and magnetic susceptibility, and density, magnetic susceptibility and seismic velocity) are used in the inversion, the variance decreases and the mean centres around the measured value of RHP (which for sample 1 was A=2.80 μmW/m³). Regarding the middle graph of FIG. 5, both of these distributions are shown in solid line as they closely overlap each other.

Similarly, as can be seen from the middle graph of FIG. 6, the likelihood distribution for RHP is initially very wide (dotted line) when only one geophysical parameter (density) is used. However, when two geophysical parameters (density and magnetic susceptibility) are used in the inversion, the variance decreases and the mean centres around the measured value of RHP (which for sample 7 was A=0.37 μmW/m³). This is shown in the dot-dashed line. Further, when three geophysical parameters (density, magnetic susceptibility and seismic velocity) are used in the inversion, the variance further decreases and the mean further centres around the measured value of RHP (which in this case was A=0.37 μmW/m³). This is shown in the solid line.

Similarly to the likelihood distribution, as can be seen from the bottom graph of FIG. 5, the posterior distribution for RHP is initially wide (dot-dashed line) when only one geophysical parameter (density) is used. However, when two or three geophysical parameters (density and magnetic susceptibility, and density, magnetic susceptibility and seismic velocity) are used in the inversion, the variance decreases and the mean centres around the measured value of RHP (which for sample 1 was A=2.80 μmW/m³). Regarding the middle graph of FIG. 5, both of these distributions are shown in solid as they closely overlap each other.

Similarly, as can be seen from the middle graph of FIG. 6, the posterior distribution for RHP is initially wide (dotted line) when only one geophysical parameter (density) is used. However, when two geophysical parameters (density and magnetic susceptibility) are used in the inversion, the variance decreases and the mean centres around the measured value of RHP (which for sample 7 was A=0.37 μmW/m³). This is shown in the dot-dashed line. Further, when three geophysical parameters (density, magnetic susceptibility and seismic velocity) are used in the inversion, the variance further decreases and the mean further centres around the measured value of RHP (which in this case was A=0.37 μmW/m³). This is shown in the solid.

Thus, FIGS. 3 to 6 demonstrate that the present inversion method for calculating RHP from geophysical parameters works effectively for just one geophysical parameter. However, they also clearly demonstrate the importance of using multiple geophysical parameters in the inversion in constraining the probability distributions for RHP toward the correct values.

It should be appreciated that in the present specification where mathematical relationships, steps and techniques are set out these should be considered to cover any trivial alteration to the relationships, steps and techniques. The skilled person would be aware that any minor/trivial/formal alteration (i.e. one that does not change the overall mathematical process used in the present invention, such as simply rearranging equations, combining equations or trivially reordering the steps) are using the same relationships, steps and techniques set out in the present specification.

It should be apparent that the foregoing relates only to the preferred embodiments of the present application and the resultant patent. Numerous changes and modification may be made herein by one of ordinary skill in the art without departing from the general spirit and scope of the invention as defined by the following claims and the equivalents thereof.

REFERENCES

Afonso, J., H. Fernandez, G. Ranalli, W. Griffin, and J. Connolly, 2008, Integrated geophysical-petrological modelling of the lithosphere and sublithosphere upper mantle: Methodology and applications: G3, 9.

Afonso, J., Fullea, J., Griffin, W., Yang, Y., Jones, A., Connolly, J. and O'Reilly, S., 2013a, 3-D multiobservable probabilistic inversion for the compositional and thermal structure of the lithosphere and upper mantle. I: a priori petrological information and geophysical observables, Journal of Geophysical Research: Solid Earth, Vol, 118, 2586-2617.

Afonso, J., Fullea, J., Yang, Y., Jones, A., and Connolly, 2013b, 3-D multi-observable probabilistic inversion for the compositional and thermal structure of the lithosphere and upper mantle. II: General methodology and resolution analysis, Journal of Geophysical Research: Solid Earth, Vol, 118, 1650-1676.

Allen, P., and J. Allen, 2005, Basin analysis: Blackwell Publishing.

SUMMARY OF THE INVENTION

Fullea, J., J. Afonso, J. Connolly, H. Fernandez, D. Garcia-Castellanos, and H. Zeyen, 2009, Lit-Mod3D: An interactive 3-D software to model the thermal, compositional, density, seismological, and rheological structure of the lithosphere and sublithospheric upper mantle: G3, 10.

McKenzie, D. P., 1978, Some remarks on the development of sedimentary basins: Earth and Planetary Science Letters, 40, 25-32.

Rybach, L., 1978, The relationship between seismic velocity and radioactive heat production in crustal rocks: An exponential law: Pure Appl. Geophys, 117, 75-82.

We claim:

1. A method of prospecting for hydrocarbons comprising calculating the radiogenic heat production (RHP) of the crust or lithosphere of a geophysical structure, wherein there is provided at least two geophysical parameters of the geophysical structure and there is a statistical dependence between the at least two geophysical parameters and the RHP of the crust or lithosphere, the method comprising:
    inverting the at least two geophysical parameters to estimate the RHP of the crust or lithosphere of the geophysical structure, wherein the RHP of the crust or lithosphere of the geophysical structure is one of at least one causes of the at least two geophysical parameters; and
    using the estimated RHP of the crust or lithosphere to calculate the surface heat flow;
    using the calculated surface heat flow to calculate temperature distributions of the geophysical structure;
    using the calculated temperature distributions of the geophysical structure to assess whether the correct conditions for hydrocarbon formation exist, or have existed, in the sedimentary layer or crust; and
    to prospect for hydrocarbons by performing drilling operations;
    wherein inverting the at least two geophysical parameters comprises selecting a forward model for each of the at least two geophysical parameters, each forward model defining a relationship between a respective one of the at least two geophysical parameters and the RHP of the geophysical structure;
    wherein the only variable in each of the respective forward models is the RHP of the geophysical structure; and
    the at least two geophysical parameters comprise at least one of magnetic susceptibility, electrical resistivity or magnetic remanence.

2. A method as claimed in claim 1, wherein there is provided calibration data comprising at least one measurement of the at least two geophysical parameters and the RHP of the geophysical structure from a sample of the geophysical structure, and wherein the method comprises optimising the forward model based on the calibration data.

3. A method as claimed in claim 1, wherein the inverting step comprises using a model in which there is statistical independence between the at least two geophysical parameters and statistical dependence between each respective geophysical parameter and the RHP of the geophysical structure.

4. A method as claimed in claim 1, wherein the at least two geophysical parameters comprise at least one electromagnetic geophysical parameter and at least one mechanical geophysical parameter.

5. A method as claimed in claim 1, wherein there is provided calibration data comprising at least one measurement of each of the at least two geophysical parameters and the RHP of the geophysical structure from one or more samples of the geophysical structure, and wherein the method comprises optimising the respective forward models based on the calibration data.

6. A method of claim 1, wherein there is provided at least one type of geophysical data of the geophysical structure, the method comprising inverting the at least one type of geophysical data to calculate the at least one geophysical parameter.

7. A method as claimed in claim 6, comprising obtaining the geophysical data.

8. A method of calculating a spatially dependent function of RHP, comprising performing the method of claim 1 pointwise for a plurality of points over the geophysical structure to calculate the RHP at each of the plurality of points, and constructing the spatially dependent function of RHP.

9. A method of calculating a basal heat flow in a geophysical structure, wherein there is provided a heat flow contribution from the mantle, the method comprising:
    calculating the RHP of the geophysical structure using the method of claim 1 over a space of geophysical structure;
    summing the RHP of at least some of the space of the geophysical structure; and
    adding the sum of the RHP to the heat flow contribution from the mantle.

10. A method of calculating surface heat flow on the Earth's surface, wherein there is provided a sediment contribution to the surface heat flow, the method comprising:
    calculating the basal heat flow using the method of claim 9, wherein the geophysical structure is the crust or lithosphere and the basal heat flow is calculated at the top of the crust or lithosphere; and
    adding the sediment contribution to the basal heat flow.

11. A method of calculating the temperature of the geophysical structure, comprising using the surface heat flow calculated using the method of claim 10.

12. A method of producing a heat and/or temperature model of a geophysical structure comprising the method of claim 1.

* * * * *